United States Patent
Halldorsson et al.

(10) Patent No.: US 9,974,668 B2
(45) Date of Patent: May 22, 2018

(54) VARIABLE TENSIONED PROSTHETIC DEVICE INCLUDING CONTINUOUSLY ELASTICIZED FABRIC

(71) Applicant: OSSUR HF, Reykjavik (IS)

(72) Inventors: Olafur Freyr Halldorsson, Reykjavik (IS); Knud Fjeldsted Rasmussen, Ikast (DK)

(73) Assignee: OSSUR HF, Reykjavik (IS)

( * ) Notice: Subject to any disclaimer, the term of this patent is extended or adjusted under 35 U.S.C. 154(b) by 33 days.

(21) Appl. No.: 14/461,744

(22) Filed: Aug. 18, 2014

(65) Prior Publication Data

US 2015/0057763 A1 Feb. 26, 2015

Related U.S. Application Data

(60) Provisional application No. 61/954,038, filed on Mar. 17, 2014, provisional application No. 61/868,341, filed on Aug. 21, 2013.

(51) Int. Cl.
*A61F 2/78* (2006.01)
*D04B 1/22* (2006.01)

(52) U.S. Cl.
CPC ............ *A61F 2/7812* (2013.01); *D04B 1/22* (2013.01); *A61F 2002/7818* (2013.01); *A61F 2250/0018* (2013.01); *D10B 2509/028* (2013.01)

(58) Field of Classification Search
CPC .. A61F 2/78; A61F 2/7812; A61F 2002/7818; A61F 2002/7837; A61F 5/0106; A61F 2013/49036; A61F 2013/49039; A61F 2013/49041; A61F 2013/49052; A61F 2013/49053; A61F 2013/49055;
(Continued)

(56) References Cited

U.S. PATENT DOCUMENTS

| 3,099,266 A | | 7/1963 | Spitzer | |
|---|---|---|---|---|
| 4,023,384 A | * | 5/1977 | Conti | D04B 9/46 66/172 E |
| 4,237,707 A | | 12/1980 | Safrit et al. | |

(Continued)

FOREIGN PATENT DOCUMENTS

WO  WO 2009003486 A1 * 1/2009 ............. A41B 9/001

OTHER PUBLICATIONS

International Search Report and Written Opinion of the International Searching Authority from International Application No. PCT/US2014/051445, dated Nov. 21, 2014.
(Continued)

*Primary Examiner* — Thomas J Sweet
*Assistant Examiner* — Christie Bahena
(74) *Attorney, Agent, or Firm* — Workman Nydegger

(57) ABSTRACT

A prosthetic device includes first and second regions divided by a longitudinal line extending between the first and second ends of the device. The device has a continuously knit elasticized fabric layer including a first set of yarns located about a circumference of the device through the first and second regions. The fabric layer has different knit structures in the first and second regions to obtain different elasticity while sharing the first set of yarns so that the first region has a first elasticity, and the second region has a second elasticity greater than the elasticity of the first region. An elastomeric layer secures an interior surface of the fabric layer.

11 Claims, 5 Drawing Sheets

(58) Field of Classification Search
CPC ... A61F 2013/49057; A61F 2250/0018; D04B 1/225; D10B 2509/028
See application file for complete search history.

(56) References Cited

U.S. PATENT DOCUMENTS

| | | | |
|---|---|---|---|
| 4,492,227 A | 1/1985 | Senn et al. | |
| 4,632,106 A | 12/1986 | Gamm | |
| 4,908,037 A | 3/1990 | Ross | |
| 4,923,474 A | 5/1990 | Klasson et al. | |
| 5,115,650 A * | 5/1992 | Patrick | A41B 11/14 66/169 A |
| 5,263,923 A | 11/1993 | Fujimoto | |
| 5,367,708 A | 11/1994 | Fujimoto | |
| 5,407,421 A | 4/1995 | Goldsmith | |
| 5,474,524 A | 12/1995 | Carey | |
| 5,640,714 A | 6/1997 | Tanaka | |
| 5,830,237 A | 11/1998 | Kania | |
| 5,888,216 A * | 3/1999 | Haberman | A61F 2/7812 623/36 |
| 6,059,834 A | 5/2000 | Springs | |
| 6,136,039 A | 10/2000 | Kristinsson et al. | |
| 6,149,690 A | 11/2000 | Belzidsky | |
| 6,282,729 B1 * | 9/2001 | Oikawa | A41D 13/015 2/465 |
| 6,485,776 B2 | 11/2002 | Janusson et al. | |
| 6,572,574 B2 | 6/2003 | Gardon-Mollard | |
| 6,592,539 B1 * | 7/2003 | Einarsson | A61F 5/0109 602/26 |
| 6,706,364 B2 | 3/2004 | Janusson et al. | |
| 6,726,641 B2 | 4/2004 | Chiang et al. | |
| 6,964,688 B1 | 11/2005 | Kania | |
| 7,025,738 B2 | 4/2006 | Hall | |
| 7,090,651 B2 | 8/2006 | Chiang et al. | |
| 7,118,602 B2 | 10/2006 | Bjarnason | |
| 7,169,189 B2 | 1/2007 | Bjarnason et al. | |
| 7,297,128 B2 | 11/2007 | Binder et al. | |
| 7,713,222 B2 | 5/2010 | Evans et al. | |
| 8,034,120 B2 | 10/2011 | Egilsson et al. | |
| 8,123,818 B2 | 2/2012 | Bjarnason et al. | |
| 2002/0183859 A1 * | 12/2002 | Houser | A61F 2/7812 623/36 |
| 2005/0101693 A1 * | 5/2005 | Arbogast | A61F 2/5046 523/122 |
| 2007/0033711 A1 | 2/2007 | Achtelstetter | |
| 2007/0043450 A1 * | 2/2007 | Pickering | A61F 2/78 623/36 |
| 2010/0274363 A1 | 10/2010 | Laghi et al. | |
| 2011/0098827 A1 | 4/2011 | Laghi et al. | |
| 2011/0208321 A1 * | 8/2011 | Doddroe | A61F 2/7812 623/36 |
| 2011/0270414 A1 | 11/2011 | Laghi et al. | |

OTHER PUBLICATIONS

Otto Bock Healthcare LP, Prosthetics—Lower Extremities, "Knee and Thigh Sleeves", retrieved from www.ottobockus.com, 1 page, Jul. 1, 2014.

Kothari, "Basics of Knitting—An Introduction," Knitting Views, Jan. 2010, pp. 20-22.

Kothari, "Basics of Knitting Knit, Tuck, and Miss Stitch," Knitting Views, Sep. 2010, pp. 22-25.

* cited by examiner

VARIABLE TENSIONED PROSTHETIC DEVICE INCLUDING CONTINUOUSLY ELASTICIZED FABRIC

TECHNICAL FIELD

The disclosure relates to a variably tensioned tubular and seamless prosthetic device, such as in sleeves or liners, formed from a continuously elasticized fabric layer having regions of different elasticity.

BACKGROUND

Common prosthetic suspension liners and sleeves are configured and dimensioned to accommodate a wide range of anatomies and movement, but may fall short at conforming to the limb of certain users with less conventional shapes and during certain joint movement. With knee joint movement, material may bunch or gather behind or posterior the knee resulting in folds in the fabric or materials of the liner or sleeve. The folds may cause discomfort as the user flexes the knee and irritate skin. The anterior side should be stretchable to permit joint movement to account for the change in the knee shape. From these observations, the anterior and posterior sides require different areas of elastic stiffness (different elasticity) to provide a comfortable liner or sleeve.

Efforts have been taken in the past to account for the different stiffness or elasticity desired from a single sleeve, such as in U.S. Pat. No. 6,592,539, granted on Jul. 15, 2003. The sleeve includes providing elasticized fabric sections having different elastic stiffness. While this sleeve successfully accommodates the anatomy and movement of various anatomies, it is labor-intensive and expensive to provide the different elastic stiffness due to the need to stitch the elasticized sections to one another.

A suspension liner described in U.S. Pat. App. Pub. No. 2011/0098827, published on Apr. 28, 2011, includes securing various fabric layers over one another at designated areas. This liner requires stitching fabric layers over one another, and providing seams along the liner which complicates the process for fabricating the liner. The additional layers also increase the overall thickness of the liner, adding weight and reducing the ability for the user to freely flex the joint covered by the liner or sleeve.

SUMMARY

The disclosure describes various embodiments of a prosthetic device, such as a suspension liner or sleeve, providing construction and design allowing for ease and low cost of comfortably accommodating a full range of anatomies and motion. The embodiments described include variable tensioned devices formed from a continuously elasticized fabric layer having regions of different elasticity for orthopedic and prosthetic applications. The solution provided by the disclosure eliminates the need for multiple fabric sections, seams or overlaid layers, and yields a flexible and thinner fabric used in a variety of applications.

The embodiments include a device and textile or fabric layer divided into at least two portions, preferably a back or posterior portion and a front or anterior portion, each having different axial elongation. Various knitting structures may obtain or adjust axial elongation in a portion of a textile or fabric layer in a continuous tubular textile. The textile or fabric layer can be employed in a variety of devices, to accommodate anatomies and motion. The device is not limited to only first and second regions, but rather may include a variety of regions arranged according to anatomical regions, function and need.

The fabric layer preferably continuously extends longitudinally and circumferentially about the liner or sleeve between first and second ends. The fabric layer may include first and second regions that stretch differently or have different elastic stiffness relative to one another. The first region may stretch more in the longitudinal direction than the second region, whereas the second region may stretch more in the transverse direction and the first region contracts in the transverse direction. The differences among the first and second regions are not limited to the aforementioned, and their elasticity may be different according to their location on the liner or sleeve. The fabric layer may have two or more regions with different degrees of stiffness.

The fabric layer is preferably continuously knit and therefore the first and second regions share various fibers, threads, yarns or filaments, referred collectively as "yarns," used to form the fabric layer. According to an embodiment, the first and second regions share the same transverse yarns, and differ in the tightness of the knit of the longitudinal yarns. The tightness may be formed by different stitch structures across the first and second regions, such that one region has a knit structure increasing elasticity whereas another region is formed by a knit structure or combination of knit structures reducing elasticity, all while at least certain yarns are shared among both the first and second regions to create the variably tensioned and continuously elasticized fabric.

In a first embodiment, a prosthetic device, such as a liner or sleeve, has first and second regions divided by a plane or longitudinal line extending between first and second ends of the device. The device includes a continuously knit elasticized fabric layer including a first set of yarns about a circumference of the device through the first and second regions. The fabric layer in the first region has a first elasticity, and the fabric layer in the second region has a second elasticity greater than the first elasticity in the first region, which results in a variable tensioned structure. An elastomeric layer may be formed along an interior surface of the fabric layer.

The device may define an arcuate profile along the longitudinal line when the device is in flexion. The first region can have a contracted conformation and the second region preferably has a stretchable conformation when the device is bent. The second region may have elasticity greater than the first region in the longitudinal direction, and the first region may have greater elasticity than the second region in the transverse direction.

The elastomeric layer may be a polymeric material continuously defined along a length and inner periphery of the fabric layer. The elastomeric material is distinguishable over a fabric because it is preferably a solid mass of material, such as silicone, that is molded to the shape of the device and fabric layer (i.e., tubular and conical forms). The elastomeric layer can have uniform properties, such as thickness, longitudinal elongation length, and axial elongation across both the first and second regions. Alternatively, the elastomeric layer is preferably tailored to have variable properties corresponding to the first and second regions, to better approximate the properties to the respective region.

The fabric layer may have a looser knit along the second region than the first region. In a variation, the first and second regions preferably share the same yarns extending circumferentially through both the first and second regions between the first and second ends. The fabric layer preferably, but not limited, defines an entire outer circumferential periphery of the device between first and second end portions, and preferably is with no seams dividing the first and second regions.

According to a variation, the first region may be formed by a plurality of knitted loop stitches and the second region may be formed by a plurality of knitted loop stitches and a plurality of tuck stitches. The second region can include a first plurality of rows consisting of knitted loop stitches alternating with a second plurality of rows including knitted loop stitches and tuck stitches. The second plurality of rows may define alternating knitted loop stitches and tuck stitches.

The first region preferably has a longitudinal elongation length 50%-70%, such as 60%, and the second region may have a longitudinal elongation length greater than the first region of at least 70% to 90%, such as 80%. An axial elongation in the first region may be 125%-175% and an axial elongation in the second region may be at least 175% to 225%.

The device may be a closed-ended conical suspension liner with the second end closed and the first end open. Alternatively, the device may be an open-ended sleeve such that the first and second ends are open and the profile of the sleeve is tubular. The curvature of each of the first and second regions is asymmetric relative to one another when the device is in flexion.

While described in a prosthetic device, the device may be used in other applications such as in orthopedic devices wherein a variably tensioned fabric may be used and formed from a continuously stitched knit fabric.

BRIEF DESCRIPTION OF DRAWINGS

These and other features, aspects, and advantages of the present disclosure will become better understood regarding the following description, appended claims, and accompanying drawings.

Figure 1:
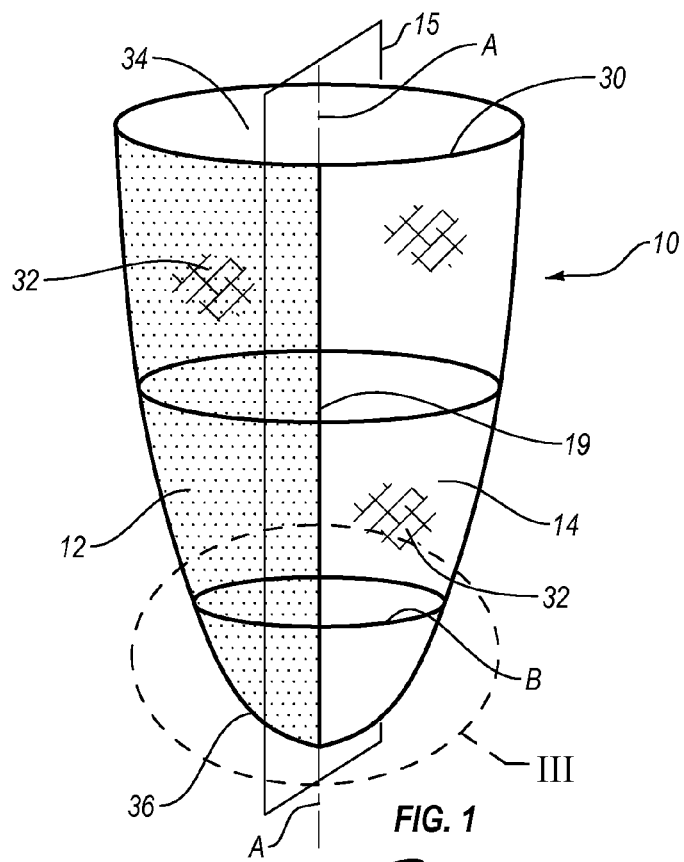
FIG. 1 is a schematic view showing a liner embodiment in a non-flexed configuration.

The drawing figures are not drawn to scale, but instead are drawn to provide a better understanding of the components, and are not intended to be limiting in scope, but to provide exemplary illustrations. The figures illustrate exemplary embodiments of a prosthetic device, and in no way limit the structures or configurations of a prosthetic device according to the present disclosure.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the embodiments disclosed, but on the contrary, that the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

A liner in suspension liners adapted to provide a soft, flexible interface between a residual limb of an amputee and a hard socket to which a prosthetic device is secured and is known in the art as exemplified by U.S. Pat. No. 4,923,474, incorporated by reference.

Such suspension liners are typically made of an air impermeable elastomer material such as silicone and may include a reinforcement layer intermediate to the inner and outer surfaces of the suspension liner body portion or externally to provide resistance against axial elongation of the elastomer constituting the suspension liner body. The reinforcement rarely restricts radial distension or stretching of the suspension liner body. A textile cover may form the outer periphery of the liner and secures to the elastomer layer. Other examples of liners are found in U.S. Pat. Nos. 6,136,039, 6,485,776, 6,706,364, 6,964,688, 7,169,189, 7,118,602 and 8,034,120, incorporated by reference.

Orthopedic or prosthetic sleeves are described in U.S. Pat. Nos. 4,908,037, 5,830,237 and 6,592,539, incorporated by reference. Such sleeves may be fabricated from elastic or elasticized materials and may support and reinforce muscles, joints and extremities of those in need of assistance and provide an airtight seal between a residual limb of an amputee and a hard socket worn by the amputee.

While various numbered regions, ends and other identified features and components are described, it will be understood the numbering is relative to the discussion on the regions, ends, identified features and components. Using numbering is not intended to refer to the same identification from embodiment to embodiment, and variations thereof.

As shown in FIG. 1, the prosthetic device 10 is a suspension liner and is divided longitudinally along a plane 15, such as an anteroposterior plane intersecting the length of the prosthetic liner into corresponding posterior and anterior sides of the liner. For simplicity, a longitudinal line 19 is defined at any location along the plane 15 to differentiate between first and second regions 12, 14 of the liner 10. The liner defines an axis A-A for defining proximal and distal ends or first and second ends of the liner. The liner 10 has a first end 34 and a second end 36, and may be conical in shape. In this embodiment, the first end 34 is open and the second end 36 is closed.

The liner 10 includes a continuous, elasticized fabric layer 32 forming a tubular shape, and extending circumferentially and along the length of the liner with no seams or additional layers. As discussed below, the fabric layer 32 is defined as being a continuously knit elasticized fabric layer because the fabric layer includes a first set of yarns 28 about a circumference of the device 10 extending through the first and second regions 12, 14. An elastomeric layer 30 is secured to an interior surface of the fabric layer 32.

The elastomeric layer may be continuously defined along a length and inner periphery of the fabric layer. The elastomeric layer can have uniform properties, such as the same thickness from longitudinal ends of the device, and longitudinal elongation length and axial elongation across both the first and second regions. Alternatively, the elastomeric layer is preferably tailored to have variable properties corresponding to the first and second regions, to better approximate the properties to the respective region.

The elastomeric material is distinguishable over a fabric because it is preferably a solid mass of material, such as silicone, that is molded to the shape of the device and fabric layer (i.e., tubular and conical forms). The elastomeric material may comprise a plurality of layers of polymeric material, and is distinguishable from a fabric layer. Examples of the elastomeric material are described in U.S. Pat. Nos. 6,136,039, 6,485,776, 6,706,364, 6,964,688, 7,169,189, 7,118,602 and 8,034,120.

The first region 12 exhibits elastic stiffness greater than the elastic stiffness of the second region 14, and forms a variable tensioned structure. In this embodiment there is a preferably single fabric layer, although the liner may be arranged with multiple fabric layers to tailor stiffness. Because there is a single fabric layer, the different stiffness or the fabric layer itself achieves elasticity of the first and second regions because the knit of the fabric layer varies across the first and second regions; there is no need to add various fabric layers by stitching to one another or layered over one another as in the prior art. The single fabric layer allows for a simple construction and design tailored to conform to the anatomy of a wearer and accommodate joint movement, while providing ease and relatively low cost for manufacture.

The fabric layer may have two or more regions with different degrees of stiffness. The regions are not limited to being divided along an anteroposterior plane, but may be divided into transverse sections, circular sections, or any other suitable sections to provide the variable elasticity required for the indication.

FIG. 1 exemplifies the liner 10 in an unflexed configuration whereas there is symmetry among the circumference of the first and second regions, corresponding to posterior and anterior portions of a leg, as separated by the line 19.

Figure 2:
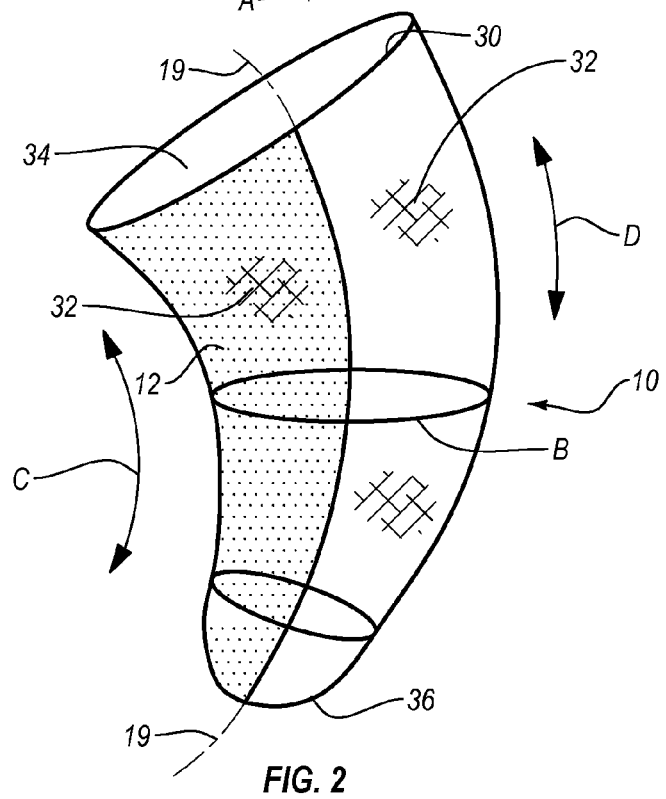
FIG. 2 is a schematic view showing the liner embodiment of FIG. 1 in a flexed configuration.

Referring to FIG. 2, the liner 10 is shown in a flexed configuration whereas the stiffness of the first region 12 stretches in the transverse direction while contracting in the longitudinal direction C to minimize any bunching or gathering of the liner behind the leg or knee. The second region stretches in the longitudinal direction D while contracting in the transverse direction B resulting in the liner forming a "banana" shape more closely mimicking a leg of a user.

The flexure of the first and second regions 12, 14 is asymmetric, with greater flexure in opposing directions (longitudinal and transverse direction) according to the region. The flexure of the second region stretches and bends to accommodate the posterior side of the leg, such as a knee, and expands to conform to the skin on the anterior side of the leg.

The contraction of the first region accommodates a reduction in the vertical dimension on the anterior side of the leg. The contraction of the first region corresponds to the "popliteal fossa" of the knee or the region on the posterior side of the knee including the bend.

Figure 3:
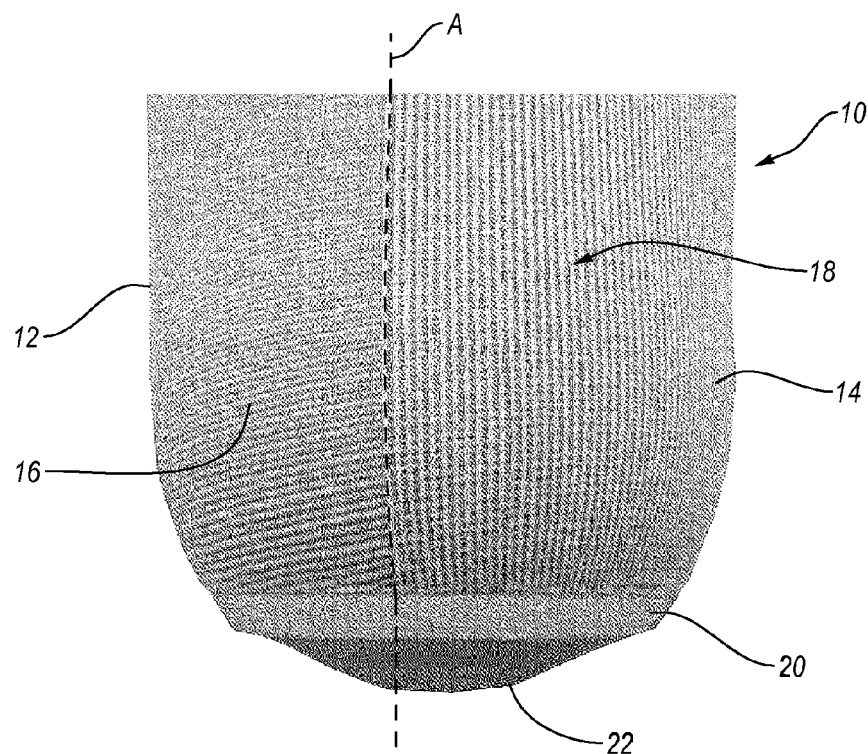
FIG. 3 is a detail view III from FIG. 1 of a distal end portion of the liner.

FIG. 3 shows an embodiment of the first and second regions 12, 14, while being part of constructing a single fabric layer, but having different knit patterns. The first region 12 has a knit pattern of tighter knit yarns 16 arranged obliquely or transversely to the dividing line A-A. The second region 14 may have a region of looser knit yarns 18, that may either be knit looser than in the first region 12, or may include a different knit 18 favoring greater elasticity in the longitudinal direction.

The liner 10 in FIG. 3 may have a reinforced distal end 20 closing the tubular shape of the liner 10, and a connection 22 may extend from the distal end and carry various connection elements known in the art of suspension liners. The first and second regions 34, 36 may extend to the distal end and come radially closer to one another as a whole, whereas the first and second regions 34, 36 expand radially away from one another as they approach the proximal, open end 36. Such connection may include a threaded portion or a pin for engaging a prosthetic lock for securing to other components. Alternatively, the liner may define a closed end portion with a continuous distal end area formed by the fabric layer, as taught in U.S. Pat. No. 8,123,818, incorporated by reference.

Embodiments of the sleeve may closely resemble those of the aforementioned suspension liner, however, the sleeve has open ends and may have a different inner layer formed or along the inner surface of the fabric layer.

Figure 4:
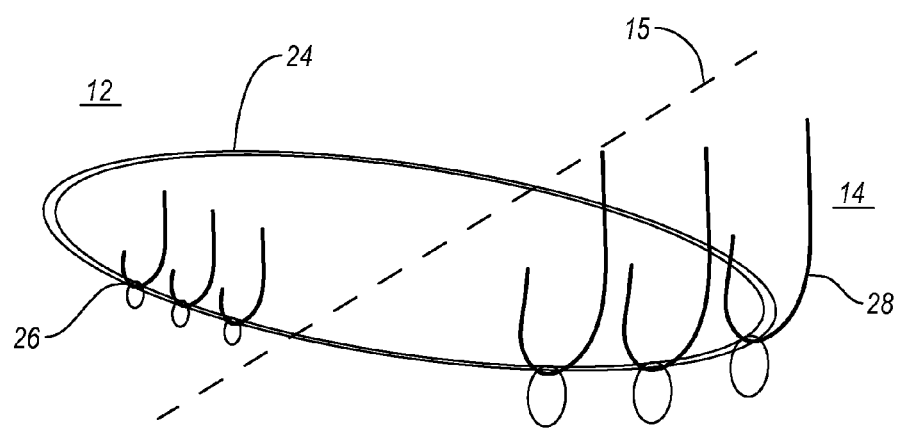
FIG. 4 is a schematic view showing different stitching patterns of first or second regions of the liner of FIG. 1.

FIG. 4 schematically shows how the yarns 26 in the longitudinal direction of the first region 12 may be more tightly knit than the yarns 28 in the second region 14. Of note, the first and second regions 12, 14 share the same transverse or circumferential yarns 24 permitting unitary and continuously knit construction of the fabric layer with regions having different stiffness.

Variations of the liner or sleeve may include a plurality of regions having different stiffness. These regions may cause the same transverse flexion about the circumference yet are distinguished in various degrees in stiffness in various longitudinal directions.

Alternatively, the transverse flexure or stiffness may vary about the circumference. The regions may be formed in localized areas only a segment short of the entire length of the liner about the anterior side corresponding to the knee. In this arrangement, the fabric layer has less stiffness at a knee region on the anterior side of the knee, yet portions above and below the knee region have greater stiffness in either the longitudinal and/or transverse directions. The posterior region of the liner may have different stiffness in the longitudinal and/or transverse directions. Even though there are regions of different stiffness, the fabric layer is continuously knit without interruptions or additional layers added upon one and the other or greater thicknesses at various portions to obtain enhanced stiffness or variable stiffness properties.

In use, the prosthetic device, either as a liner or sleeve, described may be donned over a limb by a well-known unrolling technique from a rolled up configuration to reinforce muscles and joints along desired directions of support. The liner or sleeve may be used in a knee or elbow area of a limb to provide stiffer support transversely of the knee or elbow joint in a central area while providing a softer, more elastic support in these central areas in a longitudinal direction. Likewise, end sections may provide a stiffer elastic support for the joint and limb area along the axial direction of the sleeves as compared with the transverse direction. The sleeves may be sized somewhat smaller in a relaxed state than a limb area on which the sleeve is installed, and several size sleeves can be made to accommodate a wide range of limb sizes.

Using a layer of an elastomer material, such as silicone, on the interior surface of the fabric layer enables the liner or sleeve to fit snugly against the skin of the user in a very comfortable manner due to the ability of the elastomer material to absorb and react to sheer loads between the skin and the fabric layer. The elastomer material, when in direct, airtight contact with the skin of the user holds back moisture in the skin of the user, preventing perspiration or moisture from passing into the region between the skin of the user and the sleeve. The fabric layer may be tailored to provide areas of enhanced stiffness or elasticity to cooperate with the elastomer material to augment the airtight contact.

When the sleeve is used in a prosthetic application to form a seal between the residual limb of a user and the proximal end of a prosthetic socket, the elastomer material provides an airtight seal between the skin and the prosthetic socket while the elasticized fabric layer having various regions of different elasticity provides a comfortable interface between the residual limb and the socket. Again, the sleeve will be unrolled from a rolled up condition for donning on a residual limb and will be sized somewhat smaller than a residual limb and a prosthetic socket to ensure an airtight fit between the residual limb, the sleeve and the socket.

Figure 5:
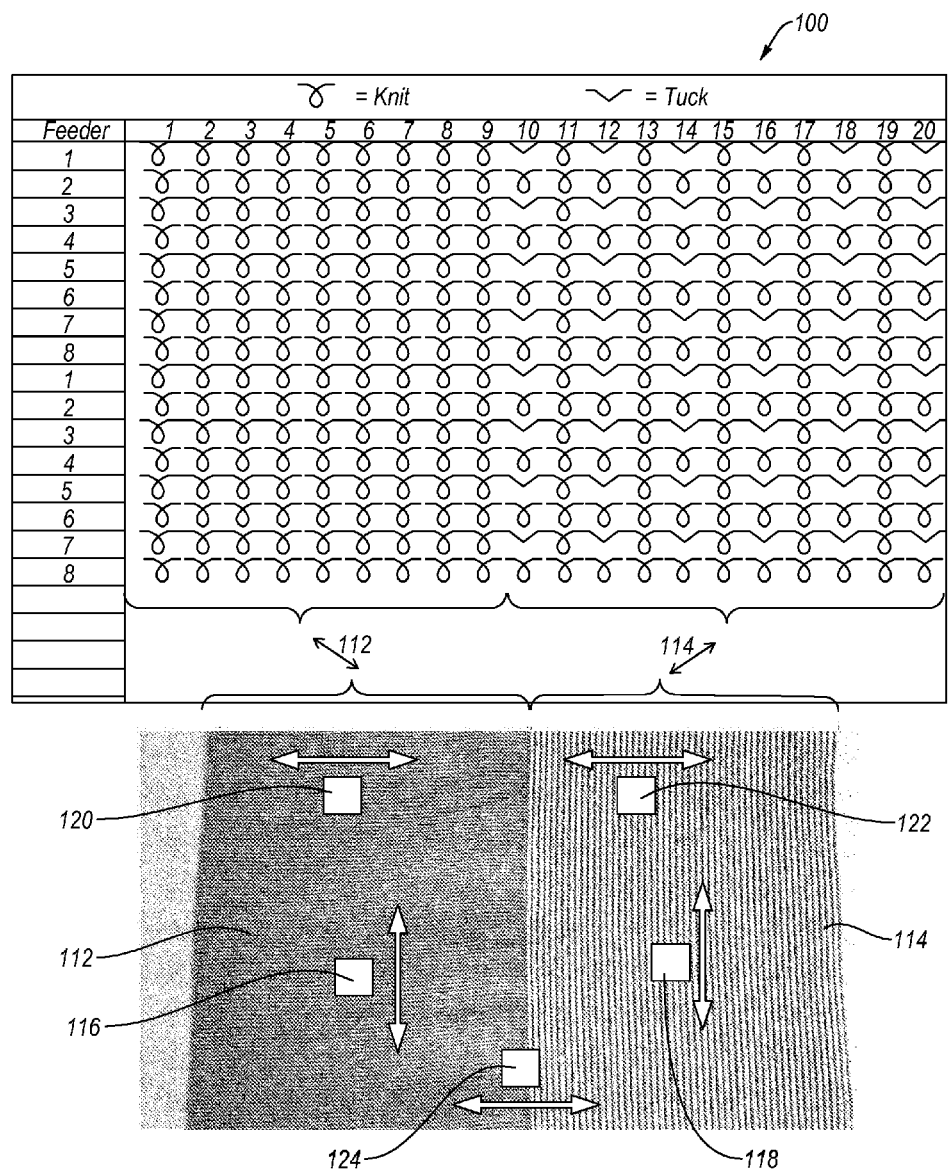
FIG. 5 is a schematic view of a first stitching structure for the textile or fabric layer of the disclosure.
Figure 6:
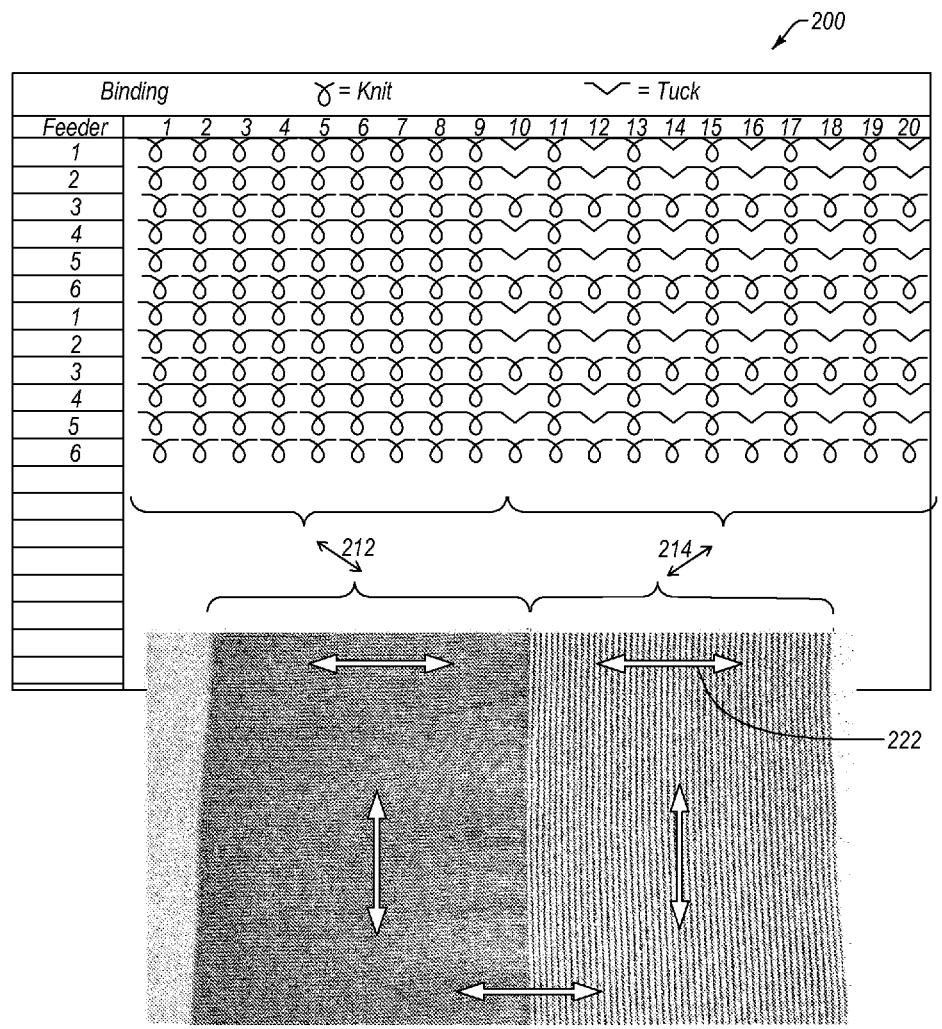
FIG. 6 is a schematic view of a second stitching structure for the textile or fabric layer of the disclosure.

FIGS. 5 and 6 show different stitching structures 100, 200 to obtain different elasticity among the first and second regions 112, 114 in a liner 10, as in the embodiment of FIG. 1. FIG. 5 illustrates a first stitching structure 100 having a "1× knit+1× tuck," such that there is an alternating pattern of one knit and one tuck along columns 10, 12, 14, 16, 18, 20 in the first region 112. Every other row of feeders having a knit in the columns is continuously knit including feeder rows 2, 4, 6. The second region 114 has a consistently knit structure across each column and feeder row located therein, and shares the same knit pattern with the first region 112 along rows 2, 4, 6.

FIG. 6 describes a second stitching structure 200 having a "1× knit+2 tuck" structure, such that there is an alternating pattern of one knit and two tucks along columns 10, 12, 14, 16, 18, 20 across the first region 212. The alternating tucks are in feeder rows 1 and 2, and 4 and 5, whereas feeder rows 3 and 6 consistently comprise the knit pattern. Like the first structure 100, the second region 214 has a consistently knit structure across each column and feeder row located therein, and the first region 212 shares the same knit pattern across feeder rows 3 and 6 to form the continuously knit structure.

In comparing the first stitching structure 100 of FIG. 5 with the second stitching structure 200 of FIG. 6, it is found that the second stitching structure 200 has less elongation in the first region 212 than the first region 112 in the first stitching structure 100 yielding a greater elongation difference between the first and second regions 212, 214.

The textile or fabric layer formed from the stitching structure may employ solely one of the first and second stitching structures, or alternatively may be formed with both of the stitching structures. The liner may include a portion with the first stitching structure at the proximal end and the second stitching structure at the distal end, and these stitching structures may be blended or joined continuously with one another by modification of different configurations of the feeder rows.

The textile or fabric layer is not limited to the first and second stitching structures, but may include many stitching structures to obtain a fabric having different regions of elasticity formed in a continuously formed textile.

In the stitching structures of FIGS. 5 and 6, the material composition of the fibers or yarns preferably includes 85% Supplex (nylon) and 15% Elastane (polyurethane), and may be colored across the different regions of the stitching structures. While Supplex may have some elasticity, Elastane provides superior elasticity and resiliency to the textile.

Different colored yarns may be used in the different regions in the stitching structures, such as the first region having a gray color, and the second region having a brown color. Other materials for the yarns may be used and the embodiments are not limited to the aforementioned materials, and may include yarns formed from polyester, polyamide, polypropylene, wool, cotton or vicose or a combination. The yarns should render a stitched structure in a manner to permit axial elongation in a portion of the textile formed by the stitching structure in a continuous tubular textile.

Referring to FIG. 5, the stitching structure may have exemplary courses per 10 cm of yarns. The first region 112 may be 90-110, whereas the exemplary courses per 10 cm of yarns in the second region 114 may be 165-195. These may be modified depending on the desired elasticity across the first and second regions. With these courses of yarns, the longitudinal elongation length 116 in the first region 112 may be 60%, and the longitudinal elongation length 118 in the second region 114 may be 80%, each because of the stitching structure. The axial elongation 120 in the first region 112 may be 150% and the axial elongation 122 in the second region 114 may be 200%, whereas the axial elongation 124 across the first and second regions 112, 114 is within the range of 150-200%.

Figure 7:
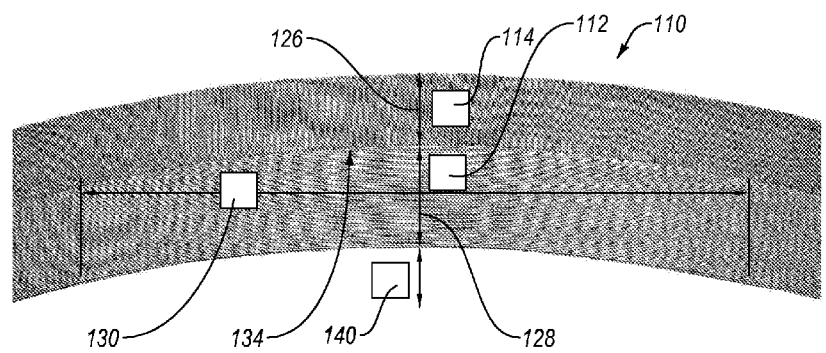
FIG. 7 is schematic view of a segment of a sleeve or liner having the stitching structure of FIG. 5.

FIG. 7 shows a side view of an exemplary liner 110 in a relaxed state having the first stitching structure of FIG. 5. The liner 110 is formed from a textile having the first stitching structure or the second stitching structure, as adapted in the discussion above, has a first width 126 across a half of the tubular liner of preferably 50-60 mm in the first region 112, and a second width 128 across a half of the tubular liner of preferably 50-60 mm in the second region 114.

FIG. 7 exemplifies how the curvature 134 is obtained over a length 130 of a segment of the liner due to the different elasticity over generally a same width of the first and second regions. Taken from a baseline of end portions of the segment, the curvature 134 extends a distance 140 into the liner. In the example given, the segment is about 500 mm and the distance is about 67 mm. If the liner 110 were constructed from a single region, the distance would be 0 with no curvature 134.

Recovery of the mechanical properties of the textile is important for repeated use by the user. Recovery of the textile includes thickness recovery for the textile to provide cushioning, and axial and longitudinal recovery after repeated expansion and reduction of the circumference of the tubular liner.

Figure 8:
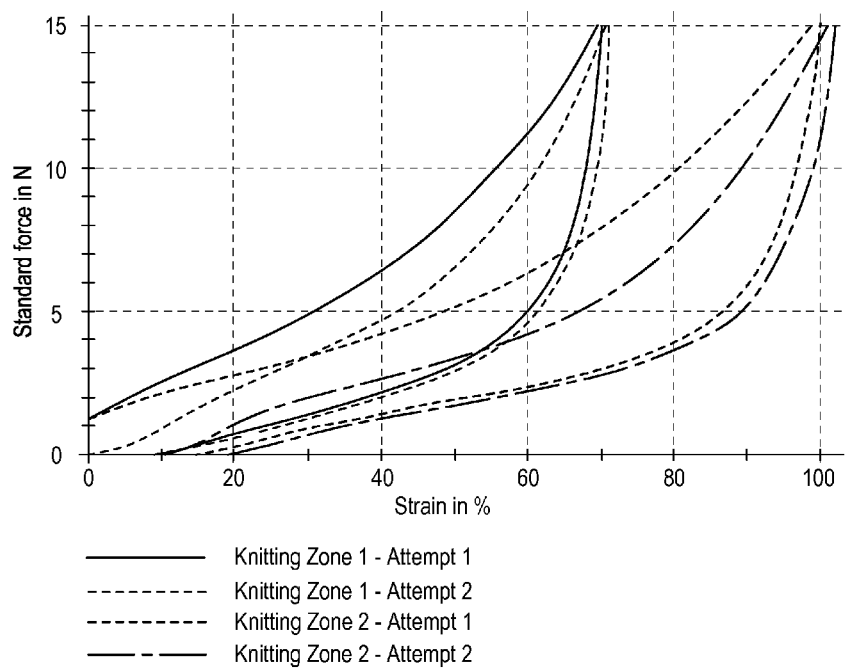
FIG. 8 is an exemplary chart showing different recovery of the textile or fabric layer having the stitching structure of FIG. 5.

FIG. 8 depicts the first and second regions as the percentage of strain over the cyclic force as an example of the recovery of mechanical properties. As shown, the strain of the first region is significantly less than the strain of the second region over the same force. Despite the difference in strain, both the first and second regions exhibit the same elongation over load curves such that the maximum strain is obtained at the highest force, and generally relaxes to at or near zero percent elongation such that the fabric as a whole generally recovers to an initial state. The second region, in part due to its increased elasticity, undergoes recovery slightly less than the first region.

The invention claimed is:

1. A prosthetic device having first and second regions generally arranged from first and second ends of the device and divided by a longitudinal line forming an anterior-posterior plane, extending between the first and second ends, the device comprising:

a continuously knit elasticized fabric layer having a tubular shape with no seam dividing the first and second regions, including a first set of yarns located about a circumference of the device through the first and second regions, the fabric layer in the first region having a first elasticity, and the fabric layer in the second region having a second elasticity greater than the elasticity in the first region;

an elastomeric layer secured to an interior surface of the fabric layer;

wherein an entire surface of the second region has greater elasticity than the first region in the longitudinal direction, such that the device defines an arcuate profile in a relaxed and unstretched state along the longitudinal line according to differences in elasticity among the first and second regions in the longitudinal direction wherein both the first and second regions are elastic in the longitudinal direction; and the second region has greater elasticity than the first region in the circumferential direction, wherein the first region is elastic in the circumferential direction;

wherein the device is a closed-ended conical liner with the second end closed and the first end open, the arcuate profile of the first and second regions is configured to be asymmetric relative to one another;

wherein the fabric layer defines an entire outer circumferential periphery of the device between first and second ends;

wherein the first and second regions have generally the same width between the first and second ends as divided by the longitudinal line;

wherein the continuously knit elasticized fabric layer comprises a plurality of circumferential first rows alternating with a plurality of circumferential second rows, the circumferential first and second rows comprising a first section corresponding to the first region and a second section corresponding to the second region, the first section of the circumferential first rows comprising only knitted loop stitches, the second section of the circumferential first rows comprising a repeating pattern of one knitted loop stitch and one tuck stitch, the circumferential second rows comprising only knitted loop stitches in both the first and second sections of the circumferential second rows;

wherein the first and second sections of the circumferential first and second rows are divided by the longitudinal line;

wherein the plurality of circumferential first rows are arranged such that in the second section the tuck stitches of the alternating pattern of each circumferential first row are longitudinally aligned with the tuck stitches of the plurality of circumferential first rows so as to form a plurality of longitudinal columns of longitudinally aligned tuck stitches, the plurality of longitudinal columns extending from the first end to the second end and parallel with the longitudinal line, the plurality of longitudinal columns of longitudinally aligned tuck stitches alternating with longitudinal columns comprising only longitudinally aligned knitted loop stitches and extending from the first end to the second end; and wherein the plurality of longitudinal columns of longitudinally aligned tuck stitches are arranged to reduce the first elasticity relative to the second elasticity such that the first region contracts relative to the second region and causes the prosthetic device to form the arcuate profile in the relaxed state and unstretched state.

2. The device of claim 1, wherein the elastomeric layer is continuously defined along a length and inner periphery of the fabric layer.

3. The device of claim 1, wherein the fabric layer has a looser knit along the second region than the first region, the first and second regions sharing the same yarns extending circumferentially through both the first and second regions.

4. The device of claim 1, wherein the first region has a longitudinal percent elongation in the range of 50%-70%, and the second region has a longitudinal percent elongation greater than the first region.

5. The device of claim 4, wherein the second region has a longitudinal percent elongation of 70% to 90%.

6. The device of claim 1, wherein a radial elongation in a circumferential direction relative to an axis of the tubular shape of the device in the first region is in the range of 125%-175%, and a radial elongation in a circumferential direction relative to the axis in the second region is in the range of 175% to 225%.

7. The prosthetic device of claim 1, wherein two consecutive circumferential first rows of the plurality of circumferential first rows alternate with a single circumferential second row of the plurality of circumferential second rows.

8. A suspension liner having first and second regions generally arranged from first and second ends of the device and divided by a longitudinal line forming an anterior-posterior plane, extending between the first and second ends, the liner comprising:

a continuously knit elasticized fabric layer having a tubular shape with no seam dividing the first and second regions, including a first set of yarns located about a circumference of the liner through the first and second regions, the fabric layer in the first region having a first elasticity, and the fabric layer in the second region having a second elasticity greater than the elasticity in the first region, the first and second regions joining at the second end defined as being closed with the first end being open;

an elastomeric layer secured to an interior surface of the fabric layer;

wherein an entire surface of the second region has greater elasticity than the first region in the longitudinal direction, wherein both the first and second regions are elastic in the longitudinal direction, and the second region has greater elasticity than the first region in the circumferential direction, wherein the first region is elastic in the circumferential direction;

wherein the liner is arranged to bend along the longitudinal line, with the liner having greater curvature along the second region compared to a curvature of the first region, such that the liner defines an arcuate profile along the longitudinal line according to differences in elasticity among the first and second regions in the longitudinal direction in a relaxed and unstretched state;

wherein the fabric layer defines an entire outer circumferential periphery of the device between first and second ends;

wherein the first and second regions have generally the same width between the first and second ends as divided by the longitudinal line;

wherein the continuously knit elasticized fabric layer comprises a plurality of circumferential first rows alternating with a plurality of circumferential second rows, the circumferential first and second rows comprising a first section corresponding to the first region and a second section corresponding to the second region, the first section of the circumferential first rows comprising only knitted loop stitches, the second section of the circumferential first rows comprising a repeating pattern of one knitted loop stitch and one tuck stitch, the circumferential second rows comprising only knitted loop stitches in both the first and second sections of the circumferential second rows;

wherein the first and second sections of the circumferential first and second rows are divided by the longitudinal line;

wherein the plurality of circumferential first rows are arranged such that in the second section the tuck stitches of the repeating pattern of each circumferential first row are longitudinally aligned with the tuck stitches of the plurality of circumferential first rows so as to form a plurality of longitudinal columns of longitudinally aligned tuck stitches, the plurality of longitudinal columns extending from the first end to the second end and parallel with the longitudinal line, the plurality of longitudinal columns of longitudinally aligned tuck stitches alternating with longitudinal columns comprising only longitudinally aligned knitted loop stitches and extending from the first end to the second end; and wherein the plurality of longitudinal columns of longitudinally aligned tuck stitches are arranged to reduce the first elasticity relative to the second elasticity such that the first region contracts relative to the second region and causes the prosthetic device to form the arcuate profile in the relaxed state and unstretched state.

9. The suspension liner of claim 8, wherein two consecutive circumferential first rows of the plurality of circumferential first rows alternate with a single circumferential second row of the plurality of circumferential second rows.

10. A prosthetic device having first and second regions generally arranged from first and second ends of the device and divided by a longitudinal line forming an anterior-posterior plane, extending between the first and second ends, the device comprising:
   a continuously knit elasticized fabric layer having a tubular shape with no seam dividing the first and second regions, including a first set of yarns located about a circumference of the device through the first and second regions, the fabric layer in the first region having a first elasticity, and the fabric layer in the second region having a second elasticity greater than the elasticity in the first region;
   an elastomeric layer secured to an interior surface of the fabric layer;
   wherein an entire surface of the second region has greater elasticity than the first region in the longitudinal direction; and
   the second region has greater elasticity than the first region in the circumferential direction, wherein the first region is elastic in the circumferential direction;
   wherein the device is a closed-ended conical liner with the second end closed and the first end open, the curvature of the first and second regions is configured to be asymmetric relative to one another;
   wherein the device defines an arcuate profile along the longitudinal line in a relaxed and unstretched state;
   wherein the first region has a longitudinal elongation length in the range of 50%-70%, and the second region has a longitudinal elongation length greater than the first region;
   wherein a radial elongation in a circumferential direction relative to an axis of the tubular shape of the device in the first region is in the range of 125%-175%, and a radial elongation in a circumferential direction relative to the axis in the second region is in the range of 175% to 225%;
   wherein the fabric layer defines an entire outer circumferential periphery of the device between first and second ends;
   wherein the first and second regions have generally the same width between the first and second ends as divided by the longitudinal line;
   wherein the continuously knit elasticized fabric layer comprises a plurality of circumferential first rows alternating with a plurality of circumferential second rows, the circumferential first and second rows each comprising a first section corresponding to the first region and a second section corresponding to the second region, the first section of the circumferential first rows comprising only knitted loop stitches, the second section of the circumferential first rows comprising a repeating pattern of one knitted loop stitch and one tuck stitch, the circumferential second rows comprising only knitted loop stitches in both the first and second sections of the circumferential second rows;
   wherein the first and second sections of the circumferential first and second rows are divided by the longitudinal line;
   wherein the plurality of circumferential first rows are arranged such that in the second section the tuck stitches of the repeating pattern of each circumferential first row are longitudinally aligned with the tuck stitches of the plurality of circumferential first rows so as to form a plurality of longitudinal columns of longitudinally aligned tuck stitches, the plurality of longitudinal columns extending from the first end to the second end and parallel with the longitudinal line, the plurality of longitudinal columns of longitudinally aligned tuck stitches alternating with longitudinal columns comprising only longitudinally aligned knitted loop stitches and extending from the first end to the second end; and
   wherein the plurality of longitudinal columns of longitudinally aligned tuck stitches are arranged to reduce the first elasticity relative to the second elasticity such that the first region contracts relative to the second region and causes the prosthetic device to form the arcuate profile in the relaxed state and unstretched state.

11. The prosthetic device of claim 10, wherein two consecutive circumferential first rows of the plurality of circumferential first rows alternate with a single circumferential second row of the plurality of circumferential second rows.

* * * * *